United States Patent [19]

Marnie et al.

[11] Patent Number: 5,573,953
[45] Date of Patent: Nov. 12, 1996

[54] METHOD FOR ENHANCING THE RESPONSE OF A BIOMIMETIC SENSOR

[75] Inventors: Glenn Marnie, Oceanside; Earl M. Dolnick, Encinitas; Ivan J. Nelson, San Diego, all of Calif.

[73] Assignee: Quantum Group, Inc., San Diego, Calif.

[21] Appl. No.: 303,357

[22] Filed: Sep. 9, 1994

[51] Int. Cl.⁶ .................................................. G01N 21/01
[52] U.S. Cl. .............................. 436/164; 436/169; 422/91; 422/82.05
[58] Field of Search .............................. 436/169, 81, 134, 436/127, 169; 422/82.05, 82.09, 82.12, 88, 91

[56] References Cited

U.S. PATENT DOCUMENTS 4,464,653  8/1984  Winner ........................................ 422/98
5,063,164  11/1991  Goldstein ................................. 436/169

*Primary Examiner*—Lyle A. Alexander
*Attorney, Agent, or Firm*—Christie, Parker & Hale, LLP

[57] ABSTRACT

The present invention provides an apparatus and method for enhancing the response of a biometric sensor for sensing toxins by measuring the rate of change of sensor readings. An LED, optically coupled to the sensor and a photodiode, transmits light through the sensor to the photodiode. The photocurrent from the photodiode is converted to a digital sensor reading value proportional to the darkness of the sensor and is loaded into a microprocessor. In the microprocessor, the sensor readings are essentially differentiated to determine the rate of change of the sensor readings. The rate of change information is used to trigger an alarm condition indicative of a predetermined level of sensed toxins.

12 Claims, 4 Drawing Sheets

METHOD FOR ENHANCING THE RESPONSE OF A BIOMIMETIC SENSOR

FIELD OF THE INVENTION

The present invention relates to a biomimetic sensor for detecting the presence of airborne toxins, and more particularly, to an apparatus and method for measuring the rate of change of optical characteristics of the sensor so that increasing or decreasing trends of the airborne toxins may be readily determined.

BACKGROUND OF THE INVENTION

A biomimetic sensor for detecting the presence of airborne toxins, such as carbon monoxide ("CO"), mercury, ethylene oxide, volatile organic materials, and hydrogen sulfide is disclosed in U.S. Pat. No. 5,063,164, the contents of which are hereby incorporated by reference. The sensor comprises a self-regenerating chemical sensor reagent impregnated into a substrate. The substrate is made of a porous solid state material which is sufficiently transmissive to light to permit detection of optical characteristics of the sensor using an optically coupled light emitting diode and photodiode.

Operating in clean air, the sensor is in an equilibrium condition indicated by a translucent yellow/orange color displayed on the sensor. If an airborne toxin such as CO is present, the sensor equilibrium is shifted as the reagent undergoes changes in its optical density, and the sensor begins to darken. After a time, which depends upon the CO concentration and the duration of exposure to CO, the sensor reaches a darkened condition that is predetermined to be an alarm point. When clear air is restored, the sensor eventually lightens to its initial orange color as it returns to the equilibrium condition.

The alarm point is a fixed point. This type of fixed alarm point, while effective, suffers from certain problems that may affect the performance of the sensor. First, even low levels of CO cause the sensor to darken appreciably if the low level condition is maintained over a long enough time. Therefore, an alarm can occur even though the level of CO may be well below a dangerous level. Even if the alarm is not triggered, the partially darkened sensor becomes more sensitive to CO and the alarm becomes susceptible to sounding based on much lower levels of CO than desired.

Second, when CO is present in sufficient concentrations and for a long enough time, the sensor darkens to the alarm condition. Depending upon the dose of CO to which the sensor is subjected, when placed in clean air, the sensor will remain dark for a considerable length of time as the sensor reagent returns to its equilibrium position. In this case, the alarm may remain energized long after a clear air condition has been established.

One skilled in the art would appreciate an apparatus and method for enhancing the response of existing biomimetic sensors. Such an apparatus and method would increase the desirability of such sensors, and make them more sensitive to actual conditions of airborne toxins.

SUMMARY OF THE INVENTION

There is provided in a presently preferred embodiment of the present invention an apparatus and method for enhancing the response of the biomimetic sensor. The invention includes the steps of intermittently measuring optical characteristics of a biomimetic sensor, differentiating a plurality of measurements over time to obtain the rate of change of the measured optical characteristics of the sensor, and determining the level of sensed toxins as a function of the rate of change of the measured optical characteristics.

Exemplary apparatus according to the present invention for implementing the method includes an LED and photodiode combination optically coupled with the biomimetic sensor. The LED illuminates the sensor, and the light transmitted through the sensor is received by the photodiode. In an analog to digital conversion, the resulting photocurrent from the photodiode, proportional to the transmitted light received by the photodiode, charges a capacitor set to a threshold value programmed into the microprocessor. The charging time of the capacitor is recorded by the microprocessor to produce a plurality of sensor readings proportional to the darkness of the sensor. Differences of adjacent readings are determined and added to an alarm register within the microprocessor. If the alarm register exceeds a predetermined value, an alarm condition is present indicating the presence of a potentially unhealthful level of toxin.

BRIEF DESCRIPTION OF THE DRAWINGS

The invention will be better understood with reference to the following detailed description and accompanying drawings wherein.

DETAILED DESCRIPTION

Figure 1:
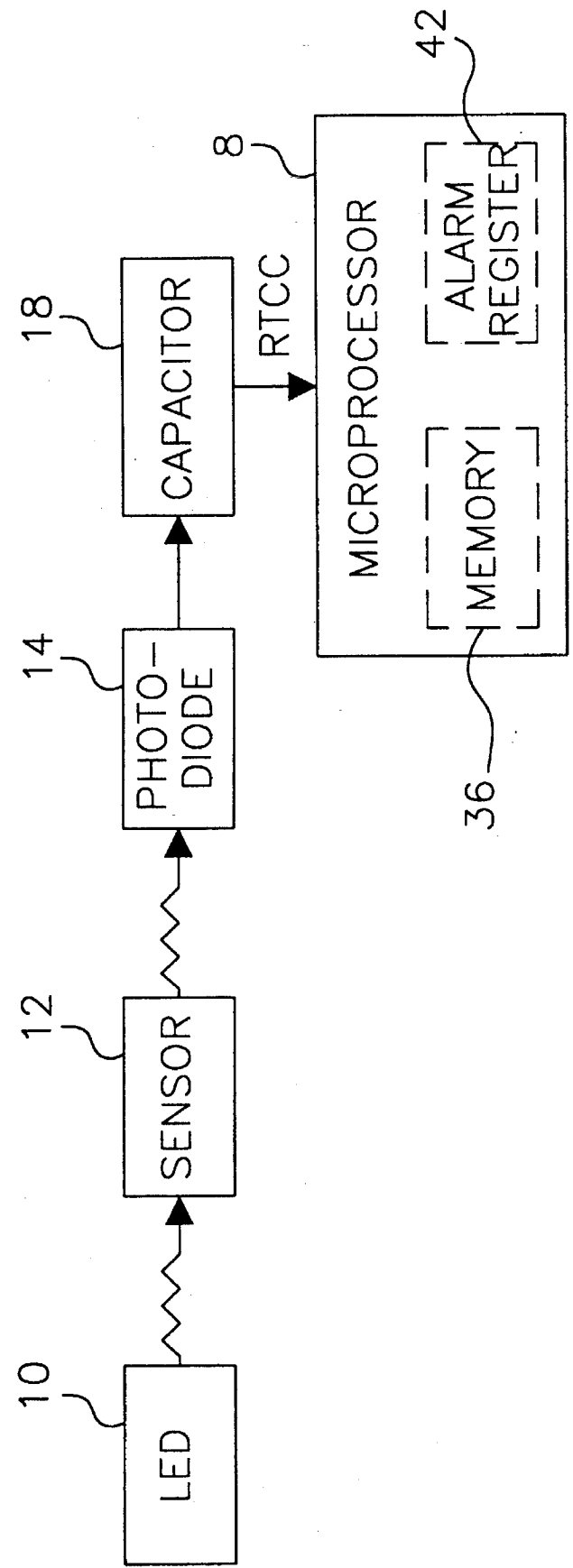
FIG. 1 is a block diagram of exemplary components of the present invention for enhancing the response of a biomimetic sensor.
Figure 3:
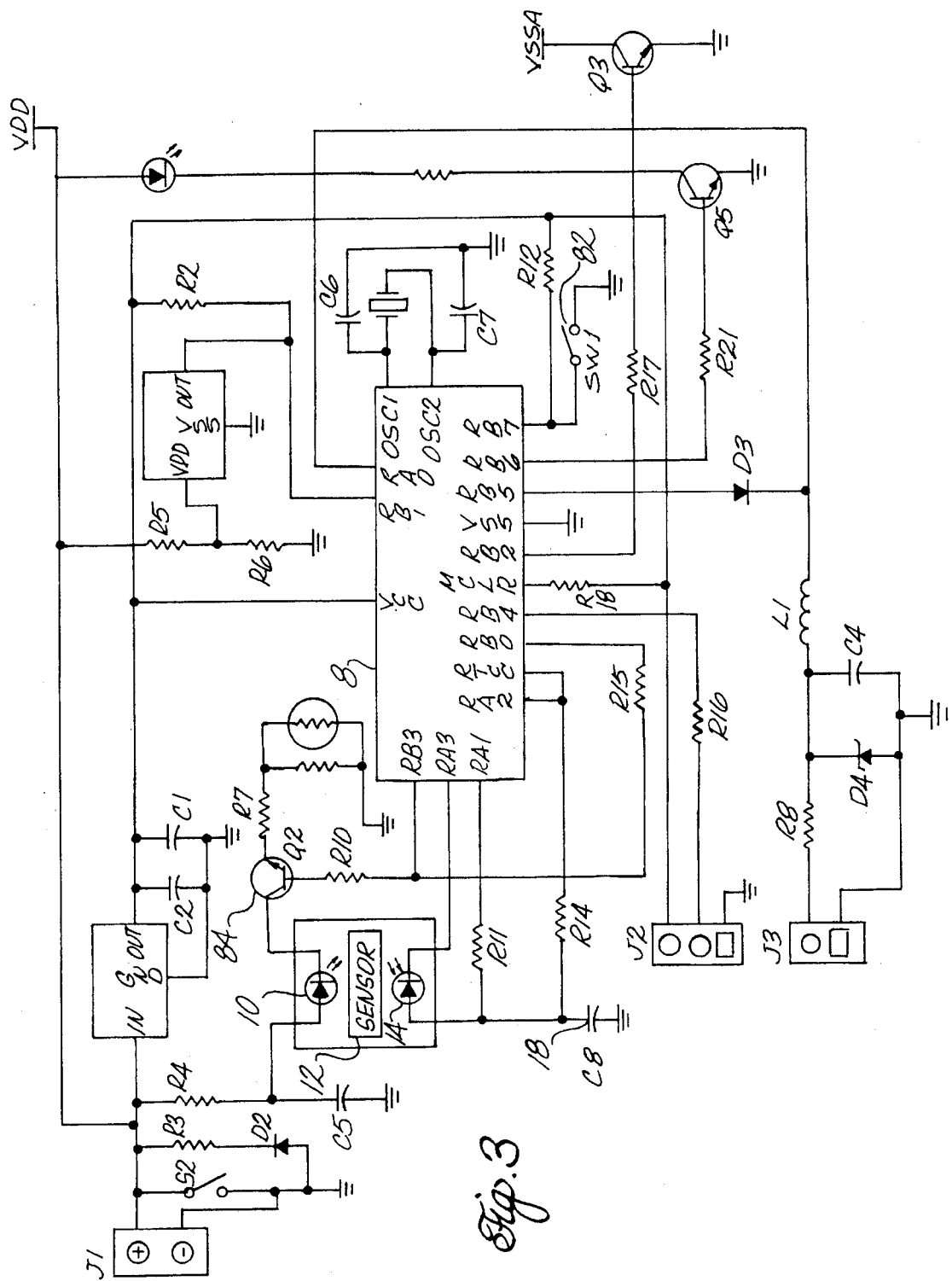
FIG. 3 is a more detailed schematic circuit diagram for implementing the present invention.

Referring to FIGS. 1 and 3, the present invention includes a microprocessor 8 and a light source, such as a light emitting diode (LED) 10 optically coupled to a biomimetic sensor 12 and a photodetector (e.g., a photodiode) 14.

In a presently preferred embodiment, the microprocessor takes sensor readings of optical characteristics of the sensor at predetermined 20 second intervals. Light from the LED is transmitted through the sensor, and the transmitted light is detected by the photodetector. The amount of transmitted light detected by the photodiode varies depending on the darkness of the sensor. As the transmitted light strikes the photodiode, the resultant photocurrent charges a capacitor 18 coupled to the photodiode. As the capacitor is charged, the microprocessor measures the duration of time from the start of the measurement to the point when the accumulated charge on the capacitor causes the potential of the capacitor to reach the threshold voltage of the RTCC pin of the microprocessor. This measurement, or sensor reading value, is a number proportional to the darkness of the sensor.

Figure 2:
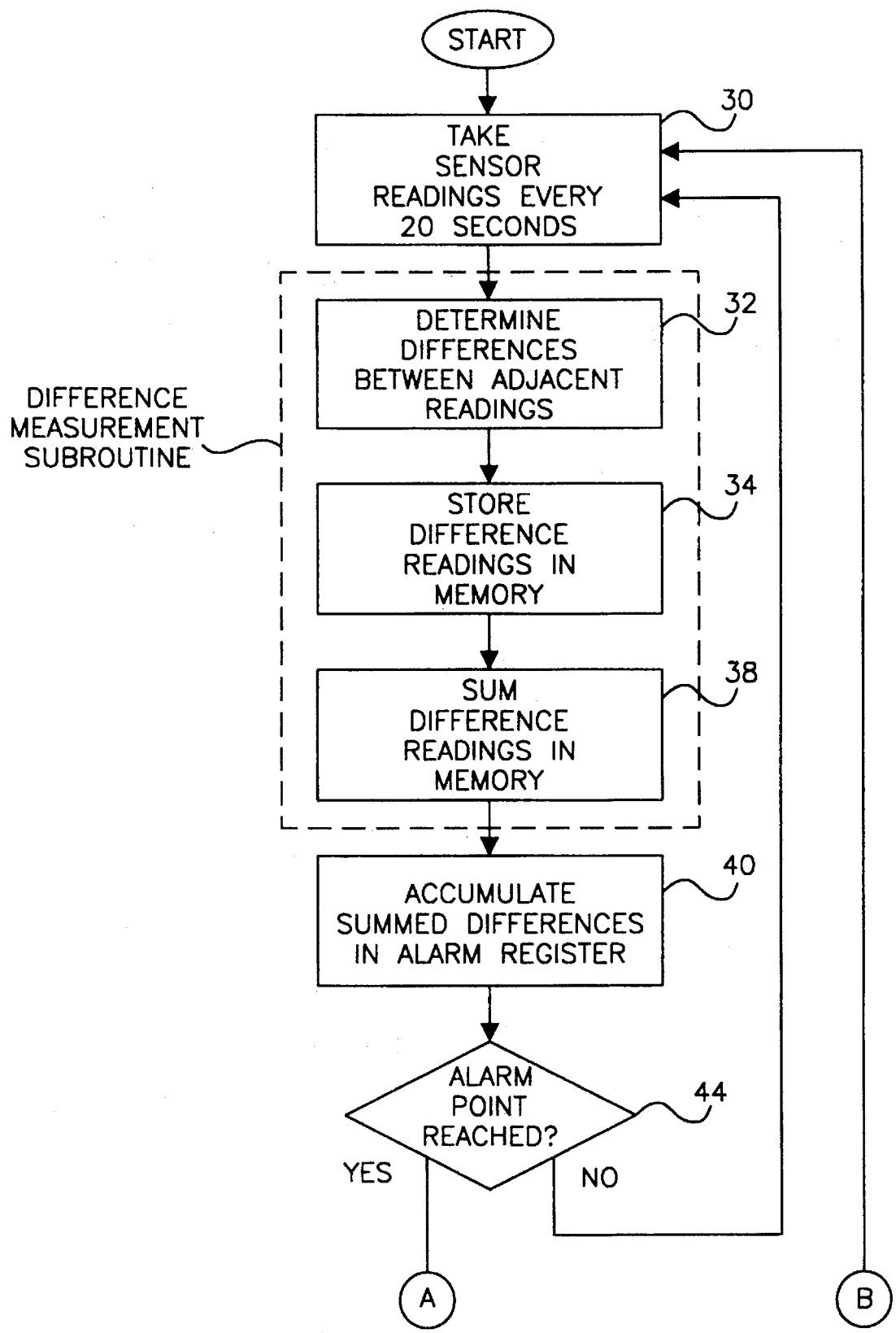
FIGS. 2 and 2a are a flow diagram illustrating steps of an exemplary method for enhancing the response of a biomimetic sensor.
Figure 2A:
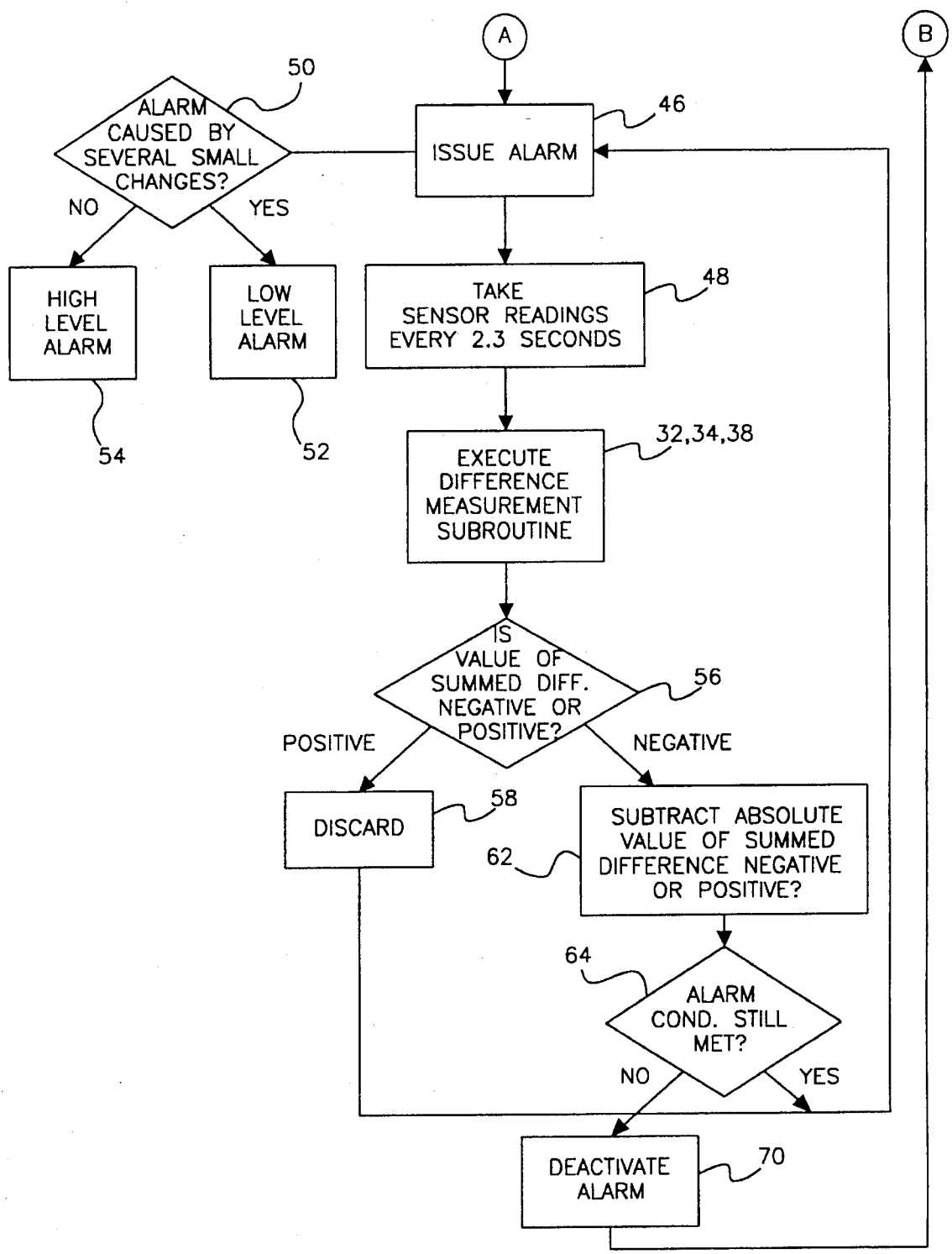

Referring also to the flow diagram of FIG. 2, as sensor readings are taken in step 30, in essence, differentiation occurs of the readings over time to determine the rate of change of optical characteristics of the sensor. Within the microprocessor, each sensor reading is subtracted in step 32 from the previous reading to produce a series of differences. The difference readings are stored in step 34 in a five location memory 36 acting as a table of differences. Once the five locations are filled, the next difference is placed in the first memory location, and the subsequent readings are sequentially transferred to the remaining memory locations. The previous reading in each location is discarded.

Every time a sensor reading is made and transferred to the microprocessor, the difference readings in memory are summed in step 38 and accumulated in step 40 in an alarm register 42. Positive differences, indicative of sensor darkening and the presence of sensed toxins such as CO, are added to the alarm register. The absolute value of negative differences, indicative of sensor lightening and the reduced presence of sensed toxins, are subtracted from the alarm register.

In exemplary operation, when CO is present, the alarm register begins to accumulate numbers. An alarm point is reached in step 44 and an alarm is issued in step 46 when the register reaches an alarm point value of $\overline{255}$. Once in alarm, the microprocessor shifts in step 48 to a rapid reading mode, accepting readings every 2.3 seconds.

One of two alarm modes is possible depending on how the alarm point was reached. If the alarm was caused in step 50 by the addition of several small difference readings, the system enters a low level alarm mode 52. If the alarm was caused by relatively few large difference readings, the system enters a high level alarm mode 54. Thus, low and high level alarms indicative of the rate of change of sensed CO can be distinguished. Once in alarm, the sensor may continue to darken but no further additions of positive differences are made to the alarm register. (Steps 56, 58)

If clean air is restored, the sensor begins to lighten. As the differences become negative, the absolute value of the negative differences are subtracted from the alarm register resulting in a reduction of the register 62 value in step 62. When the value of the alarm register falls below an alarm deactivation point value of $\overline{240}$ in step 64, the alarm is turned off in step 70 and the microprocessor again takes readings at 20 second intervals. Thus, by this method, even though the alarm may be very dark, the alarm will still shut off if the rate of sensor lightening indicates that the CO has been removed. If CO again becomes present, the alarm is reactivated as before.

In a presently preferred embodiment, the sensor reading loop and alarm reading loop operate continuously and independently. However, one skilled in the art would recognize that numerous variations to the code could be made, including programming in different languages, without departing from the scope of the invention.

By this method of operation, the level of sensed CO is determined by measuring the rate of change of light transmission through the sensor. Once the alarm is issued, only negative rates of change are recorded. Thus, the alarm condition can be deactivated well before the absolute light transmission of the sensor increases above the alarm point. Furthermore, by this method, small rates of change of light transmission can be ignored or acknowledged by a low level alarm to differentiate alarms caused by relatively low concentrations of sensed CO that exist for relatively long periods of time and more serious alarms caused by rapidly accelerating concentrations of sensed CO.

In addition to allowing for precise measurement of changes in sensor readings about the alarm point, the differential aspect of the method and apparatus by itself enhances the performance of the sensor. The absolute value of light transmission is subject to many variables, including temperature, component tolerances, battery voltage, and the like. However, since the same sensor is measured under the same conditions in the same circuit, and only the difference between successive measurements are recorded, the above effects, common to both readings, are cancelled. As an added benefit, because only differences are of interest, an absolute reference is unnecessary, thereby eliminating the need for calibration.

After every 20 cycles of successive readings, the reading portion (analog to digital converter) of the system that converts the analog signal from the capacitor to a digital sensor reading value is tested. First, the infrared LED is turned off and the microprocessor verifies that no transitions occur at the RTCC pin during a fixed time. Transitions would occur, for example, if the LED failed to turn off, or if the photodiode allowed leakage of electric current. Next, a resistor is used to provide a known current to charge the capacitor and the time to trigger the RTCC pin is measured. In proper operation, the resultant value should be within set limits. At the end of the test cycle, a value of $\overline{1}$ is subtracted from the alarm register. This prevents very low levels of toxicant from triggering a false alarm.

In a preferred embodiment, there is also a test button 82 for testing the performance of the system. When pressed, a sensor dark condition is produced by diverting a small amount of base current from the LED drive transistor 84. The accumulation routine for the alarm register is modified as the system enters an alarm state and the cycle rate is raised to 2.3 seconds in an alarm mode. The test button is set so that, in proper operation, the alarm register should reach the alarm point within 15 cycles. When the test button is released, the alarm is turned off, and the alarm register is restored to the pretest value.

In a low level alarm situation, the test button is used to silence the alarm as the value in the alarm register is divided by four. This will turn off the alarm, but if the CO continues to be present, accumulation will continue until another alarm is reached.

Those skilled in the art would readily appreciate that the scope of the invention is not limited to the presently preferred embodiment. For example, any number of properties of the sensor may be measured such as, for example, reflection of light from the sensor.

Also, one of ordinary skill in the art would recognize that any one of a variety of microprocessors and other circuit elements could be used to implement the invention.

What is claimed is:

1. A method for enhancing the response of a biomimetic sensor for sensing the presence of airborne toxins, the method comprising the steps of:

intermittently measuring optical characteristics of the sensor;

differentiating the measured characteristics to determine the rate of change of the measured characteristics of the sensor as a result of the toxins sensed by the sensor, wherein the differentiating step comprises:

making a plurality of initial readings of the sensor;

making a plurality of subsequent readings of the sensor, each subsequent reading being made a predetermined time after an adjacent initial reading;

subtracting the initial readings from adjacent subsequent readings to produce a plurality of differences; and summing a predetermined number of the differences to produce a sum of differences; and changing an alarm state as a function of the rate of change of the measured characteristics when the sum of differences differs from a predefined alarm point.

2. The method of claim 1 further comprising the step of assigning a sensor reading value to each measured characteristic, the reading being proportional to optical characteristics of the sensor.

3. The method of claim 1 wherein the measured characteristics comprise intensity of light transmitted through the sensor.

4. The method of claim 1 wherein the differentiating step further comprises:

storing the differences as entries in a table of differences; and replacing entries in the table of differences as a function of newly made readings.

5. The method of claim 4 further comprising the steps of:

summing the entries of the table of differences;

adding the summed entries in an alarm register;

entering an alarm mode when the alarm register exceeds a predefined alarm point.

6. The method of claim 5 wherein the step of entering the alarm mode comprises entering one of plurality of alarm mode levels.

7. The method of claim 5 further comprising the step of increasing rate of intermittent measurements of optical characteristics upon entry into the alarm mode.

8. The method of claim 5 wherein the step of adding the summed entries in the alarm register ceases when the alarm register exceeds the predefined alarm point.

9. A method for enhancing the response of a biomimetic sensor for sensing airborne toxins, the method comprising the steps of:

making a plurality of initial readings of the sensor;

making a plurality of subsequent readings of the sensor, each subsequent reading being made a predetermined time after an adjacent initial reading;

subtracting the initial readings from adjacent subsequent readings to produce a plurality of differences;

summing a predetermined number of the differences to produce a sum of differences; and entering an alarm mode if the sum of differences exceeds an alarm value.

10. The method of claim 9 wherein the step of entering the alarm mode comprises entering one of a plurality of alarm mode levels.

11. A method for enhancing the response of a biomimetic sensor for sensing airborne toxins, the method comprising the steps of:

making a plurality of initial readings of the sensor;

making a plurality of subsequent readings of the sensor, each subsequent reading being made a predetermined time after an adjacent initial reading;

subtracting the initial readings from adjacent subsequent readings to produce a plurality of differences;

summing at least some of the differences to produce a sum of differences; and exiting an alarm mode if the sum of differences becomes less than an alarm value.

12. The method of claim 11 wherein the step of exiting the alarm mode comprises exiting one of a plurality of alarm mode levels.

* * * * *